(12) United States Patent
Holzemann et al.

(10) Patent No.: US 6,333,308 B1
(45) Date of Patent: Dec. 25, 2001

(54) CYCLIC PEPTIDE DERIVATIVES

(75) Inventors: Gunter Holzemann, Seeheim; Claus Fittschen, Frankisch-Crumbach; Simon Goodman, Darmstadt, all of (DE)

(73) Assignee: Merck KGaA, Darmstadt (DE)

( * ) Notice: Subject to any disclaimer, the term of this patent is extended or adjusted under 35 U.S.C. 154(b) by 0 days.

(21) Appl. No.: 09/341,552
(22) PCT Filed: Dec. 15, 1997
(86) PCT No.: PCT/EP97/07048
§ 371 Date: Oct. 5, 1999
§ 102(e) Date: Oct. 5, 1999
(87) PCT Pub. No.: WO98/27112
PCT Pub. Date: Jun. 25, 1998

(30) Foreign Application Priority Data

Dec. 19, 1996 (DE) ................................. 196 53 036

(51) Int. Cl.$^7$ ................................. A61K 38/12; C07K 5/12
(52) U.S. Cl. ........................ 514/11; 530/317; 530/323; 530/330; 530/331
(58) Field of Search ..................... 514/9, 11, 18, 514/19; 530/317, 321, 323, 330, 331; 562/450

(56) References Cited

FOREIGN PATENT DOCUMENTS

93/24520 * 12/1993 (WO).
96/20216 * 7/1996 (WO).

OTHER PUBLICATIONS

Derwent Abstract XP–002064865 of Japanese Patent Application 09–278,669, Oct. 28, 1997.*

* cited by examiner

Primary Examiner—Jeffrey E. Russel
(74) Attorney, Agent, or Firm—Millen, White, Zelano & Branigan, P.C.

(57) ABSTRACT

Compounds of the formula I $$\text{cyclo-(Arg-X-Asp-R}^1\text{)} \quad \quad \text{I}$$

in which
X is Gly, Ala or NH—NH—CO,
R$^1$ is a radical of the formula II

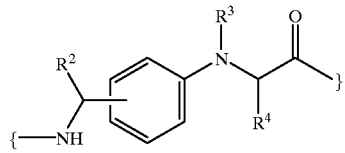

and R$^2$, R$^3$ and R$^4$ have the meanings indicated in claim 1,
and their salts,
can be used as integrin inhibitors, in particular for the prophylaxis and treatment of disorders of the circulation, in thrombosis, cardiac infarct, coronary heart disorders, arteriosclerosis, in pathological processes which are supported or propagated by angiogenesis and in tumour therapy.

31 Claims, No Drawings

SEQUENCE LISTING

```
<160> NUMBER OF SEQ ID NOS: 3

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 1

Val Arg Gly Asp
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 2

Phe Arg Gly Asp
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      cyclic peptide

<400> SEQUENCE: 3

Gly Arg Gly Asp
```

CYCLIC PEPTIDE DERIVATIVES

The invention relates to compounds of the formula I

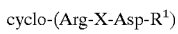

cyclo-(Arg-X-Asp-R$^1$)    I in which
X is Gly, Ala or NH—NH—CO,
where the amino acids mentioned can also be derivatized, and the amino acid residues are linked to one another in a peptide-like manner via the α-amino and α-carboxyl groups,
R$^1$ is a radical of the formula II

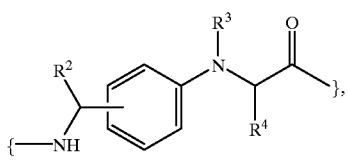

R$^2$,R$^3$,R$^4$ in each case independently of one another are H, A, Ar, R$^5$-Ar, Het or R$^5$-Het,
A is alkyl having 1–6 C atoms,
Ar is phenyl which is unsubstituted or mono-, di- or trisubstituted by R$^7$,R$^8$ or R$^9$, or unsubstituted naphthyl,
R$^5$ is alkylene having 1–6 C atoms,
R$^6$,R$^{6'}$ in each case independently of one another are H, A, benzyl or phenyl,
R$^7$,R$^8$,R$^9$ in each case independently of one another are R$^6$, OR$^6$, Hal, NO$_2$, NR$^6$R$^6$, NHCOR$^6$, CN, NHSO$_2$R$^6$, COOR$^6$ or COR$^6$,
Hal is F, Cl, Br or I and
Het is a mono- or binuclear heterocycle having 1 to 4 N, O, and/or S atoms, which can be unsubstituted or mono-, di- or trisubstituted by Hal, A, NR$^6$R$^{6'}$, CN or NO$_2$,
where, providing the residues are optically active amino acids and amino acid derivatives, both the D- and the L-forms are included,
and their salts.

Similar cyclic peptide compounds are disclosed, for example, in DE 43 10 643 or EP 0 683 173.

The invention was based on the object of discovering novel compounds having valuable properties, in particular those which can be used for the production of medicaments.

It has been found that the compounds of the formula I and their salts have very valuable pharmacological properties together with good tolerability. They act especially as integrin inhibitors, inhibiting, in particular, the interactions of the α$_v$-, β$_3$- or β$_5$-integrin receptors with ligands, such as, for example, the binding of fibrinogen to the β$_3$-integrin receptor. The compounds exhibit particular efficacy in the case of the integrins α$_v$β$_1$, α$_v$β$_3$, α$_v$β$_5$, α$_{IIb}$β$_3$ and also α$_v$β$_6$ and α$_v$β$_8$.

This action can be detected, for example, by the method which is described by J. W. Smith et al. in J. Biol. Chem. 265, 12267–12271 (1990).

The dependency of the origin of angiogenesis on the interaction between vascular integrins and extracellular matrix proteins is described by P. C. Brooks, R. A. Clark and D. A. Cheresh in Science 264, 569–71 (1994).

The possibility of the inhibition of this interaction and thus for the initiation of apoptosis (programmed cell death) of angiogenic vascular cells by a cyclic peptide is described by P. C. Brooks, A. M. Montgomery, M. Rosenfeld, R. A. Reisfeld, T.-Hu, G. Klier and D. A. Cheresh in Cell 79, 1157–64 (1994).

Compounds of the formula I which block the interaction of integrin receptors and ligands, such as, for example, of fibrinogen on the fibrinogen receptor (glycoprotein IIb/IIIa), prevent, as GPIIb/IIIa antagonists, the spread of tumour cells by metastasis. This is confirmed by the following observations: The spread of tumour cells from a local tumour into the vascular system takes place through the formation of microaggregates (microthrombi) by interaction of the tumour cells with blood platelets. The tumour cells are shielded by protection in the microaggregate and are not recognized by the cells of the immune system. The microaggregates can fix to vascular walls, whereby a further penetration of tumour cells into the tissue is facilitated. Since the formation of microthrombi is mediated by fibrinogen binding to the fibrinogen receptors on activated blood platelets, the GPIIa/IIIb antagonists can be regarded as effective metastasis inhibitors.

The compounds of the formula I can be employed as pharmaceutical active compounds in human and veterinary medicine, in particular for the prophylaxis and/or therapy of thrombosis, myocardial infarct, arteriosclerosis, inflammations, apoplexy, angina pectoris, oncoses, osteolytic diseases such as osteoporosis, pathologically angiogenic diseases such as, for example, inflammations, ophthalmological diseases, diabetic retinopathy, macular degeneration, myopia, ocular histoplasmosis, rheumatoid arthritis, osteoarthritis, rubeotic glaucoma, ulcerative colitis, Crohn's disease, atherosclerosis, psoriasis, restenosis after angioplasty, viral infection, bacterial infection, fungal infection, in acute kidney failure and in wound healing for assisting the healing process.

The compounds of the formula I can be employed as substances having antimicrobial activity in operations where biomaterials, implants, catheters or heart pacemakers are used. They have an antiseptic effect here. The efficacy of the antimicrobial activity can be demonstrated by the method described by P.Valentin-Weigund et al., in Infection and Immunity, 2851–2855 (1988).

Since the compounds of the formula I are inhibitors of fibrinogen binding and thus ligands of the fibrinogen receptors on blood platelets, they can be used as diagnostics for the detection and localization of thrombi in the vascular system in vivo, provided they are substituted, for example, by a radioactive or Uv-detectable radical.

As inhibitors of fibrinogen binding, the compounds of the formula I can also be used as efficacious medicaments for the study of the metabolism of blood platelets in different activation stages or of intracellular signal mechanisms of the fibrinogen receptor. The detectable unit of a "label" to be incorporated, e.g. an isotope labelling by $^3$H, allows the mechanisms mentioned to be investigated, after binding to the receptor.

The abbreviations of amino acid residues mentioned above and below stand for the radicals of the following amino acids:

| | |
|---|---|
| Ala | Alanine |
| AMP | Aminomethylphenyl residue |
| Asn | Asparagine |
| Asp | Aspartic acid |
| Arg | Arginine |
| Cys | Cysteine |

-continued

| | |
|---|---|
| Gln | Glutamine |
| Glu | Glutamic acid |
| Gly | Glycine |
| His | Histidine |
| homo-Phe | homo-Phenylalanine |
| Ile | Isoleucine |
| Leu | Leucine |
| Lys | Lysine |
| Met | Methionine |
| Nle | Narleucine |
| Orn | Ornithine |
| Phe | Phenylalanine |
| Phg | Phenylglycine |
| 4-Hal-Phe | 4-Halaphenylalanine |
| Pro | Proline |
| Ser | Serine |
| Thr | Threonine |
| Trp | Tryptophan |
| Tyr | Tyrosine |
| Val | Valine. |

The 3-AMP radical has the following structure:

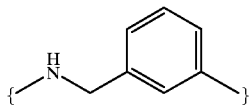

The following radicals have the meanings below:

| | |
|---|---|
| Ac | Acetyl |
| BOC | tert-Butoxycarbonyl |
| CBZ or Z | Benzyloxycarbonyl |
| DCCI | Dicyclohexylcarbodiimide |
| DMF | Dimethylformamide |
| EDCI | N-Ethyl-N,N'-dimethylaminopropyl) carbodiimide |
| Et | Ethyl |
| FCA | Fluoresceincarboxylic acid |
| Fmoc | 9-Fluorenylmethoxycarbonyl |
| HOBt | 1-Hydroxybenzotriazole |
| Me | Methyl |
| MBHA | 4-Methylbenzhydrylamine |
| Mtr | 4-Methoxy-2,3,6-trimethylphenylsulfonyl |
| HONSu | N-Hydroxysuccinimide |
| OBzl | Benzyl ester |
| OtBu | tert-Butyl ester |
| Oct | Octanoyl |
| OMe | Methyl ester |
| OEt | Ethyl ester |
| POA | Phenoxyacetyl |
| Sal | Salicyloyl |
| TFA | Trifluoroacetic acid |
| Trt | Trityl (Triphenylmethyl). |

Provided the abovementioned amino acids can occur in a number of enantiomeric forms, all these forms and also their mixtures (e.g. the DL-forms) are included above and below, e.g. as a constituent of the compounds of the formula I. Furthermore, the amino acids, e.g. as a constituent of compounds of the formula I, can be provided with appropriate protective groups known per se.

In the compounds according to the invention, so-called prodrug derivatives are also included, i.e. compounds of the formula I modified with, for example, alkyl or acyl groups, sugars or oligopeptides, which are rapidly cleaved in the body to give the active compounds according to the invention.

These also include biodegradable polymer derivatives of the compounds according to the invention, such as is described, for example, in Int. J. Pharm. 115, 61–67 (1995).

Amino acids whose configuration is not specifically indicated have the (S)- or (L)-configuration.

The invention further relates to a process for the preparation of compounds of the formula I according to claim 1, and their salts, characterized in that
 (a) a compound of the formula III

in which
 Z is -Arg-X-Asp-$R^1$-
  —X-Asp-$R^1$-Arg-
  —Asp-$R^1$-Arg-X- or
  —$R^1$-Arg-X-Asp,
 and X and $R^1$ have the meanings indicated in Claim 1, or a reactive derivative of a compound of the formula II is treated with a cyclizing agent, or
 b) a compound of the formula I is liberated from one of its functional derivatives by treating with a solvolysing or hydrogenolysing agent,
 and/or in that a basic or acidic compound of the formula I is converted into one of its salts by treating with an acid or base.

Above and below, the radicals X, $R^1$, $R^2$ $R^3$ and $R^4$ have the meanings indicated in the formulae I, II and III, if not expressly stated otherwise.

In the above formulae, alkyl is preferably methyl, ethyl, propyl, isopropyl, butyl, isobutyl, sec-butyl or tert-butyl, and further also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl.

$R^2$ and $R^3$ are, in each case independently of one another, preferably, for example, H or A, and further also Ar or $R^5$-Ar. $R^4$ is preferably, for example, H, A, Ar or $R^5$-Ar, and further also Het or $R^5$-Het. If $R^4$ is alkyl, a methylene group present in the alkyl chain can also be replaced by N, O or S.

Alkylene is preferably methylene, ethylene, propylene, butylene, pentylene or hexylene. $R^5$-Ar is preferably benzyl or phenethyl.

The amino acids and amino acid residues mentioned can also be derivatized, the N-methyl, N-ethyl, N-propyl, N-benzyl or $C_\alpha$-methyl derivatives being preferred. Derivatives of Asp and Glu are additionally preferred, in particular the methyl, ethyl, propyl, butyl, tert-butyl, neopentyl or benzyl esters of the side chain carboxyl groups, and further also derivatives of Arg, which can be substituted on the —NH—C(=NH)—$NH_2$ group by an acetyl, benzoyl, methoxycarbonyl or ethoxycarbonyl radical.

$R^6$ is preferably, for example, H, methyl or ethyl, and further benzyl or phenyl. $OR^6$ is preferably, for example, hydroxyl or methoxy. $COR^6$ is alkanoyl and is preferably formyl, acetyl, propionyl, butyryl, pentanoyl or hexanoyl.

Ar is unsubstituted, preferably—as indicated—monosubstituted phenyl, specifically preferably phenyl, o-, m-, or p-tolyl, o-, m- or p-ethylphenyl, o-, m- or p-propylphenyl, o-, m- or p-isopropylphenyl, o-, m- or p-tert-butylphenyl, o-, m- or p-trifluoromethylphenyl, o-, m- or p-hydroxyphenyl, o-, m- or p-nitrophenyl, o-, m- or p-aminophenyl, o-, m- or p-(N-methylamino)phenyl, o-, m- or p-acetamidophenyl, o-, m- or p-(trifluoromethoxy)phenyl, o-, m- or p-cyanophenyl, o-, m- or p-methoxyphenyl, o-, m- or p-ethoxyphenyl, o-, m- or p-carboxyphenyl, o-, m- or p-methoxycarbonylphenyl, o-, m- or p-ethoxycarbonylphenyl, o-, m- or p-benzyloxycarbonylphenyl, o-, m- or p-(carboxymethyloxy)phenyl, o-, m- or p-(methoxycarbonylmethyloxy)phenyl, o-, m- or p-(methoxycarbonylethyloxy)phenyl, o-, m- or p-(N,N-dimethylamino)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(difluoromethoxy)phenyl, o-, -m- or p-(fluoromethoxy)phenyl, o-, m- or p-formylphenyl, o-, m- or p-acetylphenyl, o-, m- or p-propionylphenyl, o-, m- or p-butyrylphenyl, o-, m- or p-pentanoylphenyl, o-, m- or p-(phenylsulfonamidocarbonyl)phenyl, o-, m- or p-phenoxyphenyl, o-, m- or p-methylthiophenyl, o-, m- or p-methylsulfinylphenyl, o-, m- or p-methylsulfonylphenyl or naphthyl.

Het is preferably 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3, 4-thiadiazol-2- or -5-yl, 1,2,4-thiadiazol-3- or -5-yl, 1,2,3-thiadiazol-4- or -5-yl, 2-, 3-, 4-, 5- or 6-2H-thiopyranyl, 2-, 3- or 4-4-H-thiopyranyl, 3- or 4-pyridazinyl, pyrazinyl, 2-, 3-, 4-, 5- 6- or 7-benzofuryl, 2-, 3-, 4-, 5-, 6- or 7-benzothienyl, 1-, 2-, 3-, 4-, 5-, 6- or 7-indolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl. The heterocyclic radicals can also be partially or completely hydrogenated.

Het can thus, for example, also be 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -2- or -4-imidazolyl, 2,3-dihydro-1-, -2-, -3-, -4- or -5-pyrazolyl, tetrahydro-1-, -3- or -4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl.

Amino protective group is preferably acetyl, propionyl, butyryl, phenylacetyl, benzoyl, toluyl, POA, methoxycarbonyl, ethoxycarbonyl, 2,2,2-trichloroethoxycarbonyl, BOC, 2-iodethoxycarbonyl, CBZ ("carbobenzoxy"), 4-methoxybenzyloxycarbonyl, FMOC, Mtr or benzyl.

The compounds of the formula I can have one or more chiral centres and therefore occur in various stereoisomeric forms. The formula I includes all these forms.

Accordingly, the invention relates in particular to those compounds of the formula I in which at least one of the radicals mentioned has one of the preferred meanings indicated above. Some preferred groups of compounds can be expressed by the following subformulae Ia to Ie, which correspond to the formula I and in which the radicals not described in greater detail have the meaning indicated in formula I, but in which in a) $R^2, R^3$ in each case independently of one another are H or A, $R^4$ is H, A, Ar, $R^5$-Ar, Het or $R^5$-Het and
$R^6, R^{6'}$ are H or A;

in b) $R^2, R^3$ in each case independently of one another are H or A,
$R^4$ is H, A, Ar, $R^5$-Ar, Het or $R^5$-Het
$R^6, R^{6'}$ are H or A and
Ar is phenyl which is unsubstituted or monosubstituted by $R^7$;

in c) $R^2, R^3$ in each case independently of one another are H or A,
$R^4$ is H, A, Ar, $R^5$-Ar, Het or $R^5$-Het,
$R^6, R^{6'}$ are H or A,
Ar is phenyl which is unsubstituted or monosubstituted by $R^7$ and
Het is a mononuclear aromatic or saturated heterocycle having 1 or 2 N or O atoms, which can be unsubstituted or mono- or disubstituted by Hal, A, $NR^6R^{6'}$, CN or $NO_2$;

in d) $R^2, R^3$ in each case independently of one another are H or A,
$R^4$ is H, A, Ar or $R^5$-Ar,
$R^6, R^{6'}$ are H or A and
Ar is phenyl which is unsubstituted or monosubstituted by $R^7$;

in e) X is Gly or Ala
$R^2, R^3$ in each case independently of one another are H or A,
$R^4$ is H, A, Ar or $R^5$-Ar,
$R^6, R^{6'}$ are H or A and
Ar is phenyl which is unsubstituted or monosubstituted by $R^7$.

The compounds of the formula I and also the starting substances for their preparation are otherwise prepared by methods known per se, such as are described in the literature (e.g. in the standard works such as Houben-Weyl, Methoden der organischen Chemie [Methods of Organic Chemistry], Georg-Thieme Verlag, Stuttgart), namely under reaction conditions which are known and suitable for the reactions mentioned. Use can also be made in this case of variants which are known per se, but not mentioned here in greater detail.

The starting substances, if desired, can also be formed in situ, such that they are not isolated from the reaction mixture, but immediately reacted further to give the compounds of the formula I.

Compounds of the formula I can preferably be obtained by cyclization of compounds of the formula III under the conditions of a peptide synthesis. The reaction is expediently carried out here according to customary methods of peptide synthesis, as are described, for example, in Houben-Weyl, l.c., Volume 15/II, pages 1 to 806 (1974).

The reaction preferably takes place in the presence of a dehydrating agent, e.g. of a carbodiimide such as DCCI or EDCI, and further, for example, propanephosphonic anhydride (cf. Angew. Chem. 92, 129 (1980)), diphenylphosphoryl azide or 2-ethoxy-N-ethoxycarbonyl-1,2-dihydroquinoline, in an inert solvent, e.g. a halogenated hydrocarbon such as dichloromethane, an ether such as tetrahydrofuran or dioxane, an amide such as DMF or dimethylacetamide, a nitrile such as acetonitrile, in dimethyl sulfoxide or in the presence of mixtures of these solvents, at temperatures between approximately −10 and 40, preferably between 0 and 30°. In order to promote intramolecular cyclization before intermolecular peptide bonding, it is expedient to work in dilute solutions. The reaction time, depending on the conditions used, is between a few minutes and 14 days.

Instead of compounds of the formula III, derivatives of compounds of the formula III, preferably a preactivated carboxylic acid, or a carboxylic acid halide, a symmetrical or mixed anhydride or an active ester can also be employed. Radicals of this type for the activation of the carboxyl group in typical acylation reactions are described in the literature (e.g. in the standard works such as Houben-Weyl, Methoden der organischen Chemie [Methods of Organic Chemistry], Georg-Thieme Verlag, Stuttgart).

Activated esters are expediently formed in situ, e.g. by addition of HOBt or N-hydroxysuccinimide.

As a rule, the reaction is carried out in an inert solvent, using a carboxylic acid halide in the presence of an acid-binding agent, preferably of an organic base such as triethylamine, dimethylaniline, pyridine or quinoline. The addition of an alkali metal or alkaline earth metal hydroxide, carbonate or bicarbonate or of another salt of a weak acid of the alkali metals or alkaline earth metals, preferably of potassium, sodium, calcium or caesium, may also be favourable.

As a rule, the starting substances of the formula III are new. They can be prepared by known methods of peptide synthesis.

The compounds of the formula I can further be obtained by liberating them from their functional derivatives by solvolysis, in particular hydrolysis, or by hydrogenolysis.

Preferred starting substances for solvolysis or hydrogenolysis are those which, instead of one or more free amino and/or hydroxyl groups, contain corresponding protective amino and/or hydroxyl groups, preferably those which, instead of an H atom which is bonded to an N atom, carry an amino protective group, e.g. those which correspond to the formula I, but instead of an $NH_2$ group contain an NHR' group (in which R' is an amino protective group, e.g. BOC or CBZ).

Starting substances are further preferred which, instead of the H atom of a hydroxyl group, carry a hydroxyl protective group, e.g. those which correspond to the formula I, but instead of a hydroxyphenyl group contain an R"O-phenyl group (in which R" is a hydroxyl protective group).

A number of—identical or different—protected amino and/or hydroxyl groups can also be present in the molecule of the starting substance. If the protective groups present differ from one another, they can be selectively removed in many cases.

The expression "amino protective group" is generally known and relates to groups which are suitable for protecting (for blocking) an amino group from chemical reactions, but which are easily removable after the desired chemical reaction has been carried out at other positions in the molecule. Typical groups of this type are, in particular, unsubstituted or substituted acyl, aryl, aralkoxymethyl or aralkyl groups. Since the amino protective groups are removed after the desired reaction (or reaction sequence), their nature and size is otherwise not critical; however, those having 1–20, in particular 1–8 C atoms, are preferred. The expression "acyl group" is to be interpreted in the widest sense in connection with the present process. It includes acyl groups derived from aliphatic, araliphatic, aromatic or heterocyclic carboxylic acids or sulfonic acids, such as, in particular, alkoxycarbonyl, aryloxycarbonyl and especially aralkoxycarbonyl groups. Examples of acyl groups of this type are alkanoyl such as acetyl, propionyl, butyryl; aralkanoyl such as phenylacetyl; aroyl such as benzoyl or toluyl; aryloxyalkanoyl such as POA; alkoxycarbonyl such as methoxycarbonyl, ethoxycarbonyl, 2,2,2-trichloroethoxycarbonyl, BOC, 2-iodoethoxy-carbonyl; aralkyloxycarbonyl such as CBZ ("carbobenzoxy"), 4-methoxybenzyloxycarbonyl, FMOC; arylsulfonyl such as Mtr. Preferred amino protective groups are BOC and Mtr, and further CBZ, Fmoc, benzyl and acetyl.

The expression "hydroxyl protective group" is likewise generally known and relates to groups which are suitable for protecting a hydroxyl group from chemical reactions, but which are easily removable after the desired chemical reaction has been carried out at other positions in the molecule. Typical of such groups are the abovementioned unsubstituted or substituted aryl, aralkyl or acyl groups, and further also alkyl groups. The nature and size of the hydroxyl protected groups is not critical, since they are removed again after the desired chemical reaction or reaction sequence; groups having 1–20, in particular 1–10 C atoms, are preferred. Examples of hydroxyl protective groups are, inter alia, benzyl, p-nitrobenzoyl, p-toluenesulfonyl, tert-butyl and acetyl, benzyl and tert-butyl being particularly preferred. The COOH groups in aspartic acid and glutamic acid are preferably protected in the form of their tert-butyl esters (e.g. Asp(OBut)).

The liberation of the compounds of the formula I from their functional derivatives is carried out—depending on the protective group used—for example, with strong acids, expediently with TFA or perchloric acid, but also with other strong inorganic acids such as hydrochloric acid or sulfuric acid, strong organic carboxylic acids such as trichloroacetic acid or sulfonic acids such as benzene- or p-toluenesulfonic acid. The presence of an additional inert solvent is possible, but not always necessary. Suitable inert solvents are preferably organic solvents, for example carboxylic acids such as acetic acid, ethers such as tetrahydrofuran or dioxane, amides such as DMF, halogenated hydrocarbons such as dichloromethane, and further also alcohols such as methanol, ethanol or isopropanol, and also water. Mixtures of the abovementioned solvents are also possible. TFA is preferably used in an excess without addition of a further solvent, perchloric acid in the form of a mixture of acetic acid and 70% strength perchloric acid in the ratio 9:1. The reaction temperatures for the cleavage are expediently between approximately [lacuna] and approximately 50°; the reaction is preferably carried out between 15 and 30° (room temperature).

The groups BOC, OBut and Mtr can be removed, for example, preferably using TFA in dichloromethane or using approximately 3 to 5N HCl in dioxane at 15–30°; the FMOC group using an approximately 5 to 50% solution of dimethylamine, diethylamine or piperidine in DMF at 15–30°.

The trityl group is employed for the protection of the amino acids histidine, asparagine, glutamine and cysteine. The cleavage is carried out, depending on the desired final product, using TFA/10% thiophenol, the trityl group being removed from all amino acids mentioned; when using TFA/anisole or TFA/thioanisole, the trityl group is removed only His, Asn and Gln, while it remains on the Cys side chain.

Hydrogenolytically removable protective groups (e.g. CBZ or benzyl) can be removed, for example, by treating with hydrogen in the presence of a catalyst (e.g. of a noble metal catalyst such as palladium, expediently on a support such as carbon). Suitable solvents here are those indicated above, in particular, for example, alcohols such as methanol or ethanol or amides such as DMF. As a rule, the hydrogenolysis is carried out at temperatures between approximately 0 and 100° and pressures between approximately 1 and 200 bar, preferably at 20–30° C. and 1–10 bar. Hydrogenolysis of the CBZ group takes place, for example, readily on 5 to 10% Pd/C in methanol or with ammonium formate (instead of hydrogen) on Pd/C in methanol/DMF at 20–30°.

A base of the formula I can be converted into the associated acid addition salt using an acid, for example by reaction of equivalent amounts of the base and of the acid in an inert solvent such as ethanol and subsequent evaporation. For this reaction, suitable acids are in particular those which yield physiologically acceptable salts. Thus inorganic acids can be used, e.g. sulfuric acid, nitric acid, hydrohalic acids such as hydrochloric acid or hydrobromic acid, phosphoric acids, such as orthophosphoric acid, sulfamic acid, and further organic acids, in particular aliphatic, alicyclic, araliphatic, aromatic or heterocyclic mono- or polybasic carboxylic, sulfonic or sulfuric acids, e.g. formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, ascorbic acid, nicotinic acid, isonicotinic acid, methane- or ethanesulfonic acid, ethanedisulfonic acid, 2-hydroxyethanesulfonic acid, benzenesulfonic acid, p-toluenesulfonic acid, naphthalenemono- and disulfonic acids, and laurylsulfuric acid. Salts with physiologically unacceptable acids, e.g. picrates, can be used for the isolation and/or purification of the compounds of the formula I.

On the other hand, an acid of the formula I can be converted into one of its physiologically acceptable metal or ammonium salts by reaction with a base. Possible salts here are in particular the sodium, potassium, magnesium, calcium and ammonium salts, and also substituted ammonium salts, e.g. the dimethyl, diethyl or diisopropylammonium salts, monoethanol-, diethanol- or diisopropylammonium salts, cyclohexyl- or dicyclohexylammonium salts, dibenzylethylenediammonium salts, and furthermore, for example, salts with arginine or lysine.

The invention further relates to the use of the compounds of the formula I and/or their physiologically acceptable salts for the production of pharmaceutical preparations, in particular by a non-chemical route. In this context, they can be brought into a suitable dosage form together with at least one solid, liquid and/or semisolid excipient or auxiliary and, if appropriate, in combination with one or more further active compounds.

The invention further relates to pharmaceutical preparations comprising at least one compound of the formula I and/or one of its physiologically acceptable salts.

These preparations can be used as medicaments in human or veterinary medicine. Suitable excipients are organic or inorganic substances which are suitable for enteral (e.g. oral) or parenteral administration, topical application or for administration in the form of an inhalation spray and do not react with the novel compounds, for example water, vegetable oils, benzyl alcohols, alkylene glycols, polyethylene glycols, glycerol triacetate, gelatine, carbohydrates such as lactose or starch, magnesium stearate, talc and petroleum jelly. In particular, tablets, pills, coated tablets, capsules, powders, granules, syrups, juices or drops are used for oral administration, suppositories are used for rectal administration, solutions, preferably oily or aqueous solutions, and also suspensions, emulsions or implants are used for parenteral administration, and ointments, creams or powders are used for topical application. The novel compounds can also be lyophilized and the lyophilizates obtained used, for example, for the production of injection preparations. The preparations indicated can be sterilized and/or can contain auxiliaries such as lubricants, preservatives, stabilizers and/or wetting agents, emulsifiers, salts for affecting the osmotic pressure, buffer substances, colorants, flavourings and/or one or more other active compounds, e.g. one or more vitamins.

For administration as an inhalation spray, sprays can be used which contain the active compound either dissolved or suspended in a propellant gas or propellant gas mixture (e.g. $CO_2$ or chlorofluorohydrocarbons). The active compound is expediently used here in micronized form, it being possible for one or more additional physiologically tolerable solvents to be present, e.g. ethanol.

Inhalation solutions can be administered with the aid of customary inhalers.

The compounds of the formula I and their physiologically acceptable salts can be used as integrin inhibitors in the control of illnesses, in particular of thromboses, cardiac infarct, coronary heart disorders, arteriosclerosis, tumours, osteoporosis, inflammations and infections.

The compounds of the formula I according to claim 1 and/or their physiologically acceptable salts are also used in pathological processes which are supported or propagated by angiogenesis, in particular in tumours or rheumatoid arthritis.

In this case, the substances according to the invention can as a rule be administered in analogy to other known, commercially available peptides, but in particular in analogy to the compounds described in U.S. Pat. No. 4,472,305, preferably in doses of between approximately 0.05 and 500 mg, in particular between 0.5 and 100 mg per dose unit. The daily dose is preferably between approximately 0.01 and 2 mg/kg of body weight. The specific dose for each patient depends, however, on all sorts of factors, for example on the efficacy of the specific compound employed, on the age, body weight, general state of health, sex, on the diet, on the time and route of administration, on the excretion rate, pharmaceutical combination and severity of the particular disorder to which the therapy relates. Parenteral administration is preferred.

The compounds of the formula I can further be used as integrin ligands for the preparation of columns for affinity chromatography for the preparation of integrins in pure form.

The ligand, i.e. a compound of the formula I, is in this case covalently coupled to a polymeric support via an anchor function, e.g. the carboxyl group of Asp.

Suitable polymeric support materials are the polymeric solid phases known per se in peptide chemistry, preferably having hydrophilic properties, for example crosslinked polysugars such as cellulose, Sepharose or Sephadex®, acrylamides, polymers based on polyethylene glycol or Tentakel polymers®.

The preparation of the materials for affinity chromatography for integrin purification is carried out under conditions such as are customary and known per se for the condensation of amino acids.

The compounds of the formula I contain one or more chiral centres and can therefore be present in racemic or in optically active form. Racemates obtained can be separated into the enantiomers mechanically or chemically by methods known per se. Preferably, diastereomers are formed from the racemic mixture by reaction with an optically active resolving agent. Suitable resolving agents are, for example, optically active acids, such as the D- and L-forms of tartaric acid, diacetyltartaric acid, dibenzoyltartaric acid, mandelic acid, malic acid, lactic acid or the various optically active camphorsulfonic acids such as β-camphorsulfonic acid. An enantiomer separation with the aid of a column packed with an optically active resolving agent (e.g.

dinitrobenzyolphenylglycine) is also advantageous; suitable eluents are, for example, a mixture of hexane/isopropanol/acetonitrile, e.g. in the volume ratio 82:15:3.

Of course, it is also possible to obtain optically active compounds of the formula I by the methods described above by using starting substances which are already optically active.

Above and below, all temperatures are indicated in ° C. In the following examples, "customary working up" means: if necessary, water is added, the mixture is adjusted, if necessary, to a pH of between 2 and 10 depending on the constitution of the final product, and extracted with ethyl acetate or dichloromethane, the organic phase is separated off, dried over sodium sulfate and evaporated, and the residue is purified by chromatography on silica gel and/or by crystallization. $R_f$ values on silica gel; eluents: ethyl acetate/methanol 9:1. RT=retention time (minutes) on HPLC in the following systems:

[A]

Column: Lichrosorb®RP 18 (250×4; 5 µm);

Eluent A: 0.1% TFA in water

Eluent B: 0.1% TFA in 90% acetonitrile, 10% water

Flow rate: 1 ml/min

Gradient: 20–95% B/50 min

Detection at 215 nm.

The diastereomers are preferably separated under the conditions indicated.

Mass spectrometry (MS): FAB (Fast Atom Bombardment) $(M+H)^+$

EXAMPLE 1

Equimolar amounts of methyl (R,S)-2-bromo-2-phenylacetate and 3-hydroxymethylaniline are reacted to give methyl N-(3-hydroxymethylphenyl)aminophenylacetate. By reaction with thionyl chloride to give methyl N-(3-chloromethylphenyl)aminophenylacetate and subsequent reaction with sodium azide, methyl N-(3-azidomethylphenyl)aminophenylacetate ("A") is obtained. A solution of 9.2 g of "A" in 350 ml of ethyl acetate is hydrogenated for 35 minutes in the presence of 1 g of Pd/C (5%). After removing the catalyst and the solvent, methyl N-(3-aminomethylphenyl)aminophenyl-acetate) ("B") is obtained as an oil, RT 19.5; FAB 271.

By reaction of "B" with benzyl anhydride, methyl N-(3-benzyloxycarbonylaminomethyl-phenyl) aminophenylacetate is obtained, which is then hydrolyzed in KOH/methanol to give N-(3-benzyloxycarbonylaminomethylphenylacetic acid (=N-(Z-3-AMP)-aminophenylacetic acid). By reaction with 1 equivalent in each case of H-Arg(Mtr)-Gly-OtBu, DCCI and HOBt in dichloromethane, Z-3-AMP-Phg-Arg(Mtr)-Gly-OtBu is obtained. The removal of the Z-protective group is carried out as described above by catalytic hydrogenation; subsequent peptide coupling with BOC-Asp(OBzl)-3-AMP-Phg-Arg(Mtr)-Gly-OtBu. After removal of the BOC protective group and of the tert-butyl ester in HCl/dioxane, H-Asp (OBzl)-3-AMP-Phg-Arg(Mtr)-Gly-OH- is obtained, and, after cyclization, the compound Cyclo-(Asp(OBzl)-3-AMP-Phg-Arg(Mtr)-Gly). After hydrolysis of the ester, removal of the Mtr protective group in 98% trifluoroacetic acid, purification and separation by means of HPLC, cyclo-(Asp-3-AMP-L-Phg-Arg-Gly) and cyclo-(Asp-3-AMP-D-Phg-Arg-Gly) are obtained.

The two compounds are characterized as follows:

RT 15.5 FAB 567 and RT 12.5 FAB 567, the assignment for the two diastereomers being open to question.

Analogously, the following are obtained starting from 2-bromo-3-methylbutyric acid cyclo-(Asp-3-AMP-L-Val-Arg-Gly) (SEQ ID NO: 1) and cyclo-(Asp-3-AMP-D-Val-Arg-Gly), from 2-bromoacetic acid cyclo-(Asp-3-AMP-Gly-Arg-Gly) (SEQ ID NO: 3) and from 2-bromo-3-phenylpropionic acid cyclo-(Asp-3-AMP-L-Phe-Arg-Gly) (SEQ ID NO: 2) and cyclo-(Asp-3-AMP-D-Phe-Arg-Gly).

The following examples relate to pharmaceutical preparations:

EXAMPLE A

Injection vials

A solution of 100 g of an active compound of the formula I and 5 g of disodium hydrogenphosphate is adjusted to pH 6.5 in 3 l of double-distilled water using 2 N hydrochloric acid, sterile-filtered, dispensed into injection vials, lyophilized under sterile conditions and sealed aseptically. Each injection vial contains 5 mg of active compound.

EXAMPLE B

Suppositories

A mixture of 20 g of an active compound of the formula I is fused with 100 g of soya lecithin and 1400 g of cocoa butter, poured into moulds and allowed to cool. Each suppository contains 20 mg of active compound.

EXAMPLE C

Solution

A solution of 1 g of an active compound of the formula I, 9.38 g of $NaH_2PO_4$. 2 $H_2O$, 28.48 g of $Na_2HPO_4$. 12 $H_2O$ and 0.1 g of benzalkonium chloride in 940 ml of double-distilled water is prepared. The pH is adjusted to 6.8, and the solution is made up to 1 l and sterilized by irradiation. This solution can be used in the form of eye drops.

EXAMPLE D

Ointment 500 mg of an active compound of the formula I are mixed with 99.5 g of petroleum jelly under aseptic conditions.

EXAMPLE E

Tablets

A mixture of 1 kg of active compound of the formula I, 4 kg of lactose, 1.2 kg of potato starch, 0.2 kg of talc and 0.1 kg of magnesium stearate is compressed to give tablets in the customary manner such that each tablet contains 10 mg of active compound.

EXAMPLE F

Coated tablets

Analogously to Example E, tablets are pressed which are then coated in a customary manner with a coating of sucrose, potato starch, talc, tragacanth and colorant.

EXAMPLE G

Capsules 2 kg of active compound of the formula I are dispensed into hard gelatine capsules in the customary manner such that each capsule contains 20 mg of the active compound.

EXAMPLE H

Ampoules

A solution of 1 kg of active compound of the formula I in 60 l of double-distilled water is sterile-filtered, dispensed into ampoules, lyophilized under sterile conditions and aseptically sealed. Each ampoule contains 10 mg of active compound.

EXAMPLE I

Inhalation spray 14 g of active compound of the formula I are dissolved in 10 l of isotonic NaCl solution and the solution is dispensed into commercially available spray containers having a pump mechanism. The solution can be sprayed into the mouth or nose. One burst of spray (approximately 0.1 ml) corresponds to a dose of approximately 0.14 mg.

$R^1$ is a radical of the formula II

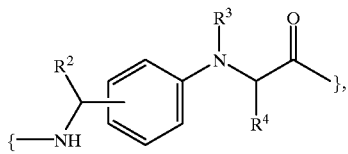

$R^2, R^3, R^4$ in each case independently of one another are H, A, Ar, $R^5$-Ar, Het or $R^5$-Het, wherein if $R^4$ is A, a methylene group present therein can be replaced by N, O or S, A is alkyl having 1–6 C atoms,

---

---

What is claimed is:

1. A compound of the formula I $$\text{cyclo-(Arg-X-Asp-}R^1\text{)} \qquad \qquad \text{I}$$

in which

X is Gly, Ala or NH—NH—CO, where the amino acids mentioned can also be derivatized, and the amino acid residues are linked to one another in a peptide-like manner via the α-carboxyl groups, Ar is phenyl which is unsubstituted or mono-, di- or trisubstituted by $R^7$, $R^8$ or $R^9$, or is unsubstituted naphthyl, $R^5$ is alkylene having 1–6 C atoms, $R^6, R^{6'}$ in each case, independently of one another, are H, A, benzyl or phenyl, $R^7, R^8, R^9$ in each case, independently of one another, are $R^6$, $OR^6$, Hal, $NO_2$, $NR^6R^{6'}$, $NHCOR^6$, CN, $NHSO_2R^6$, $COOR^6$ or $COR^6$, Hal is F, Cl, Br or I, and Het is a mono- or binuclear heterocycle having 1 to 4 N, O, and/or S atoms, which can be unsubstituted or mono-, di- or trisubstituted by Hal, $NR^6R^{6'}$, A, CN or $NO_2$, wherein optically active amino acids and amino acid derivatives can be present in either their D- or L-forms, or a salt thereof.

2. A compound according to claim 1, wherein said compound is in the form of an enantiomer.

3. A compound according to claim 1, wherein said compound is
   a) cyclo-(Arg-Gly-Asp-3-AMP-L-Phg) or a salt thereof;
   b) cyclo-(Arg-Gly-Asp-3-AMP-D-Phg) or a salt thereof;
   c) cyclo-(Arg-Gly-Asp-3-AMP-L-Val) (SEQ ID NO: 1) or a salt thereof;
   d) cyclo-(Arg-Gly-Asp-3-AMP-D-Val) or a salt thereof;
   e) cyclo-(Arg-Gly-Asp-3-AMP-Phe) (SEQ ID NO: 2) or a salt thereof;
   f) cyclo-(Arg-Gly-Asp-3-AMP-D-Phe) or a salt thereof; or
   g) cyclo-(Arg-Gly-Asp-3-AMP-Gly) (SEQ ID NO: 3) or a salt thereof.

4. A process for the preparation of a compound according to claim 1, comprising:
   a) treating a compound of formula III

H—Z—OH      III in which
   Z is -Arg-X-Asp-$R^1$-
   —X-Asp-$R^1$-Arg-
   —Asp-$R^1$-Arg-X- or
   —$R^1$-Arg-X-Asp,
   or a reactive derivative of a compound of the formula III with a cyclizing agent; or
   b) liberating a compound of formula I from one of its functional derivatives by treatment with a solvolyzing or hydrogenolyzing agent;
   and/or converting a basic or acidic compound of formula I into one of its salts by treatment with an acid or base.

5. A process for production of a pharmaceutical preparation comprising combining at least one compound of the formula I according to claim 1 or a physiologically acceptable salt thereof with at least one solid, liquid or semiliquid excipient or auxiliary.

6. A pharmaceutical composition comprising at least one compound of the formula I according to claim 1 or a physiologically acceptable salt thereof and at least one solid, liquid or semiliquid excipient or auxiliary.

7. A method for treating a patient suffering from thromboses, cardiac infarct, a coronary heart disorder, arteriosclerosis, a tumor, osteoporosis, an inflammation or an infection, comprising administering an effective amount of an intregrin inhibitor compound according to claim 1.

8. A method of treating a patient suffering from a pathological condition which is supported or propagated by angiogenesis, comprising administering an effective amount of a compound according to claim 1.

9. A compound according to claim 1, wherein said compound is in the form of a diastereomer.

10. A compound according to claim 1, wherein A is methyl, ethyl, propyl, isopropyl, butyl, isobutyl, sec-butyl or tert-butyl.

11. A compound according to claim 1, wherein X is Gly or an N-methyl, N-ethyl, N-propyl, N-benzyl, or $C_\alpha$-methyl derivative thereof; Ala or an N-methyl, N-ethyl, N-propyl, N-benzyl or $C_\alpha$-methyl derivative thereof; or NH—NH—CO.

12. A compound according to claim 1, wherein $R^6$ is H, methyl, ethyl, benzyl or phenyl.

13. A compound according to claim 1, wherein $COR^6$ is formyl, acetyl, propionyl, butyryl, pentanoyl or hexanoyl.

14. A compound according to claim 1, wherein $R^2$ and $R^3$ are each independently H or A; $R^4$ is H, A, Ar, $R^5$-Ar, Het or $R^5$-Het; and $R^6$ and $R^{6'}$ are each independently H or A.

15. A compound according to claim 1, wherein $R^2$ and $R^3$ are each independently H or A; $R^4$ is H, A, Ar, $R^5$-Ar, Het or $R^5$-Het; $R^6$ and $R^{6'}$ are each independently H or A; and Ar is phenyl which is unsubstituted or monosubstituted by $R^7$.

16. A compound according to claim 1, wherein $R^2$ and $R^3$ are in each case, independently of one another, H or A; $R^4$ is H, A, Ar, $R^5$-Ar, Het or $R^5$-Het; and $R^6$ and $R^{6'}$ are each independently H or A; Ar is phenyl which is unsubstituted or monosubstituted by $R^7$; and Het is a mononuclear aromatic or saturated heterocycle having 1 or 2 N or O atoms, which can be unsubstituted or mono- or disubstituted by Hal, A, $NR^6R^{6'}$, CN or $NO_2$.

17. A compound according to claim 1, wherein $R^2$ and $R^3$ are in each case, independently of one another, H or A; $R^4$ is H, A, Ar or $R^5$-Ar; $R^6$ and $R^{6'}$ are H or A; and Ar is phenyl which is unsubstituted or monosubstituted by $R^7$.

18. A compound according to claim 1, wherein X is Gly or Ala, $R^2$ and $R^3$ are in each case, independently of one another, H or A; $R^4$ is H, A, Ar or $R^5$-Ar; $R^6$ and $R^{6'}$ are H or A; and Ar is phenyl which is unsubstituted or monosubstituted by $R^7$.

19. A compound according to claim 1, wherein $R^2$,$R^3$ and $R^4$ are each independently H, A, Ar, or $R^5$-Ar, wherein if $R^4$ is A, a methylene group therein can be replaced by N, O or S.

20. A compound according to claim 11, wherein $R^2$,$R^3$ and $R^4$ are each independently H, A, Ar, or $R^5$-Ar, wherein if $R^4$ is A, a methylene group therein can be replaced by N, O or S.

21. A pharmaceutical composition according to claim 6, wherein said composition contains 0.5–100 mg of a compound of formula I or a physiologically acceptable salt thereof.

22. A method according to claim 7, wherein said compound is administered in an amount of 0.01–2 mg/kg of body weight per day.

23. A pharmaceutical composition preparation comprising at least one compound of the formula I according to claim 11 or a physiologically acceptable salt thereof and at least one solid, liquid or semiliquid excipient or auxiliary.

24. A method for treating a patient suffering from thromboses, cardiac infarct, a coronary heart disorder, arteriosclerosis, a tumor, osteoporosis, an inflammation or an infection, comprising administering an effective amount of an intregrin inhibitor compound according to claim 11.

25. A method of treating a patient suffering from a pathological condition which is supported or propagated by angiogenesis, comprising administering an effective amount of a compound according to claim 11.

26. A pharmaceutical composition preparation comprising at least one compound of the formula I according to claim 18 or a physiologically acceptable salt thereof and at least one solid, liquid or semiliquid excipient or auxiliary.

27. A method for treating a patient suffering from thromboses, cardiac infarct, a coronary heart disorder, arteriosclerosis, a tumor, osteoporosis, an inflammation or an infection, comprising administering an effective amount of an intregrin inhibitor compound according to claim 18.

28. A method of treating a patient suffering from a pathological condition which is supported or propagated by angiogenesis, comprising administering an effective amount of a compound according to claim 18.

29. A pharmaceutical composition preparation comprising at least one compound of the formula I according to claim 20 or a physiologically acceptable salt thereof and at least one solid, liquid or semiliquid excipient or auxiliary.

30. A method for treating a patient suffering from thromboses, cardiac infarct, a coronary heart disorder, arteriosclerosis, a tumor, osteoporosis, an inflammation or an infection, comprising administering an effective amount of an intregrin inhibitor compound according to claim 20.

31. A method of treating a patient suffering from a pathological condition which is supported or propagated by angiogenesis, comprising administering an effective amount of a compound according to claim 20.

* * * * *